United States Patent [19]

Honda et al.

[11] 4,320,668
[45] Mar. 23, 1982

[54] SUB-LANCE ASSEMBLY FOR SAMPLING AND TEMPERATURE-MEASURING OF MOLTEN METAL DURING REFINING THEREOF

[75] Inventors: Akira Honda, Kamakura; Shinobu Kumagai; Hiroyuki Takita, both of Yokohama, all of Japan

[73] Assignee: Nippon Kokan Kabushiki Kaisha, Tokyo, Japan

[21] Appl. No.: 127,217

[22] Filed: Mar. 4, 1980

[30] Foreign Application Priority Data

Mar. 28, 1979 [JP] Japan .................................. 54-35663

[51] Int. Cl.³ .............................................. G01N 1/12
[52] U.S. Cl. .............................. 73/863.11; 73/864.31
[58] Field of Search ........... 73/423 R, 863.11, 864.31; 266/225, 226; 285/134

[56] References Cited

U.S. PATENT DOCUMENTS

| | | | |
|---|---|---|---|
| 2,626,166 | 1/1953 | Fawick | 285/134 |
| 3,166,344 | 1/1965 | Davis | 285/134 |
| 3,559,623 | 2/1971 | Decamps | 266/225 |
| 3,581,948 | 6/1971 | Detalle | 222/603 |
| 3,598,380 | 8/1971 | Jilek et al. | 73/343 |
| 4,141,249 | 2/1979 | Ishikawa | 73/421 B |

Primary Examiner—S. Clement Swisher
Attorney, Agent, or Firm—Frishauf, Holtz, Goodman and Woodward

[57] ABSTRACT

A sub-lance assembly for sampling and temperature-measuring of a molten metal during refining thereof in a top-blowing oxygen converter, which comprises: a sub-lance having a concentric three-pipe structure comprising a gas supply pipe, a water supply pipe and a water discharge pipe with said gas supply pipe as the center, said sub-lance being rotatably and releasably fitted to a sub-lance carriage in the substantially vertical position; a probe fitted to the lowermost end of said gas supply pipe, for sampling and temperature-measuring of a molten metal during refining thereof; an inner cylinder fixed to the upper end portion of said sub-lance; an outer cylinder, having a water supply branch pipe and a water discharge branch pipe, rotatably engaging with said inner cylinder, said outer cylinder being connected to said sub-lance carriage; said water supply pipe, said inner cylinder, said outer cylinder and said water supply branch pipe communicating with each other in a water-tight manner, said water discharge pipe, said inner cylinder, said outer cylinder and said water discharge branch pipe communicating with each other in a water-tight manner; a drive mechanism, fitted onto the outer surface of said outer cylinder, for rotating said sub-lance around the axial line thereof; and, a sub-lance rotation angle detector, fitted to the tip of the axle of rotation of said drive mechanism, for detecting the angle of rotation of said sub-lance.

4 Claims, 5 Drawing Figures

FIG. 1
PRIOR ART
FIG. 5
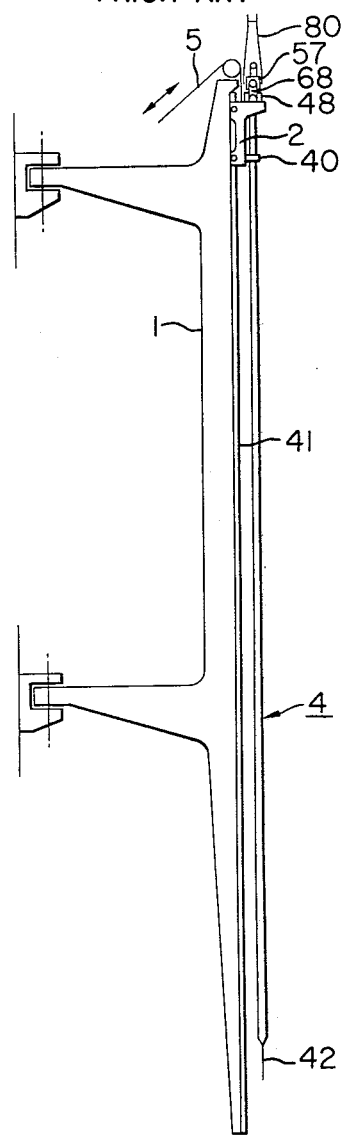
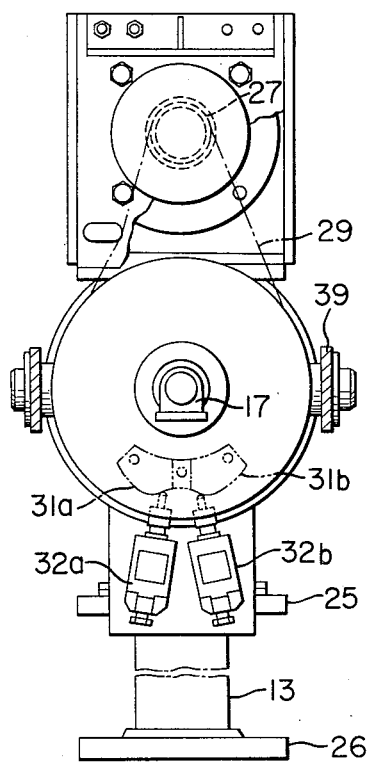

SUB-LANCE ASSEMBLY FOR SAMPLING AND TEMPERATURE-MEASURING OF MOLTEN METAL DURING REFINING THEREOF

REFERENCE TO PATENTS, APPLICATIONS AND PUBLICATIONS PERTINENT TO THE INVENTION

A prior document pertinent to the present invention is U.S. Pat. No. 4,141,249 dated Feb. 27, 1979, which corresponds to Japanese Patent Provisional Publication No. 112,204/78 dated Sept. 30, 1978 and Japanese Utility Model Provisional Publication No. 126,910/78 dated Oct. 7, 1978.

The content of the prior art disclosed in the above-mentioned prior document is described under the caption of the "BACKGROUND OF THE INVENTION" presented hereafter.

FIELD OF THE INVENTION

The present invention relates to a sub-lance assembly for sampling and temperature-measuring of a molten metal during refining thereof in a top-blowing oxygen converter.

BACKGROUND OF THE INVENTION

In the field of refining of molten metal in a top-blowing oxygen converter, a control system based on dynamic control has been developed for the purpose of saving labor in refining operations and automating the processes. A sub-lance for obtaining information and data concerning conditions of refining in the converter such as the chemical composition and the temperature of molten metal during refining is indispensable for said control system.

Refining of a molten metal in a top-blowing converter is effected by inserting a main lance for blowing oxygen substantially vertically and downwardly into a top-blowing oxygen converter containing a molten metal to be refined, to blow pressurized oxygen onto the surface of the molten metal through the main lance at a certain position above the surface of the molten metal. On the other hand, sampling and temperature-measuring of the molten metal during refining in the converter are carried out by inserting a sub-lance into the converter substantially vertically and downwardly at a proper timing, and by immersing a probe for sampling and temperature-measuring of molten metal, which is releasably fitted to the lowermost end of the sub-lance, into the molten metal.

In general, the sub-lance is releasably fitted to a sub-lance carriage. The sub-lance carriage is suspended by a wire rope engaging with a block provided at the upper end portion of a turning frame, and moves vertically together with the sub-lance along a guide rail provided vertically on the turning frame by hoisting up or down said wire rope with the use of a winch. Sampling and temperature-measuring of the molten metal during in the converter are therefore conducted by lowering the sub-lance together with the sub-lance carriage by hoisting down the wire rope with the use of the winch, and immersing the probe fitted to the lowermost end of the sub-lance into the molten metal. The sub-lance is movable, as required, together with the sub-lance carriage, from outside to above the converter and from above the converter to outside, by turning the turning frame, for such purposes as replacement of the prove, maintenance and inspection of the sub-lance and replacement of the sub-lance.

The sub-lance usually has a concentric three-pipe structure comprising from inside to outside a gas supply pipe, a water discharge pipe and a water supply pipe, and is cooled by cooling water flowing through the water supply pipe and the water discharge pipe, during sampling and/or temperature-measuring of the molten metal. To prevent slag from coming into the probe when the probe passes through the slag layer convering the surface of the molten metal, a pressurized gas such as air and nitrogen gas is blown into the probe through the gas supply pipe.

However, the sub-lance inserted into the converter during refining of the molten metal deflects inevitably toward the main lance under the effect of the high temperature heat of the hot spot where occur reactions between oxygen blown from the main lance and the molten metal and the high temperature heat of molten metal and molten slag splashing and adhering onto the sub-lance. More specifically, the sub-lance deflects toward the main lance, under the effect of the above-mentioned heat affection, substantially in proportion to the number of repetitions of sampling and/or temperature-measuring during refining of the molten metal. Because of this deflection, it has been unavoidable that the following problems occurred in a conventional sub-lance after being used several times:

(1) It becomes difficult to immerse straight vertically the probe fitted to the lowermost end of the sub-lance into the molten metal, and this causes troubles in sampling and/or temperature-measuring;

(2) The sub-lance and the probe become too close to the hot spot, or even come in the hot spot, thus causing burnout of the sub-lance and the probe;

(3) The device for engaging and disengaging the probe with the lowermost end of the sub-lance becomes unserviceable; and (4) It becomes impossible for the sub-lance to pass through a through-hole provided in a hood which hangs over and covers the converter, and when the aforementioned deflection of the sub-lance is serious, it may become necessary to remove the sub-lance by flamecutting.

To avoid these inconveniences, prevention of the above-mentioned deflection of the sub-lance toward the main lance has been attempted through such measures as the enhancement of cooling of the sub-lance and the prevention of molten metal and molten slag from adhering onto the sub-lance. It was however impossible to ensure prevention of the aforementioned deflection of the sub-lance through these measures.

With a view to solving the above-mentioned problems involved in the conventional sub-lance, in U.S. Pat. No. 4,141,249 dated February, 1979, which corresponds to Japanese Patent Provisional Publication No. 112,204/78 dated Sept. 30, 1978 and Japanese Utility Model Provisional Publication No. 126,910/78 dated Oct. 7, 1978, there is proposed a sub-lance assembly for sampling and temperature-measuring of molten metal during refining thereof in a top-blowing oxygen converter, which comprises: a sub-lance having a concentric three-pipe structure comprising from inside to outside a gas supply pipe, a water discharge pipe and a water supply pipe; a water supply outer cylinder having a water supply branch pipe, rotatably engaging with the upper end portion of said water supply pipe; a water discharge outer cylinder having a water discharge branch pipe, rotatably engaging with the upper end portion of said water discharge pipe; said water supply branch pipe and said water discharge branch pipe being integrally connected together by a fixing plate; a drive mechanism fitted onto the outer surface of said water supply outer cylinder or said water discharge outer cylinder, for rotating said sub-lance around the axial line thereof; and a sub-lance rotation angle detector fitted to the tip of the axle of rotation of said drive mechanism, for detecting the angle of rotation of said sub-lance (hereinafter referred to as the "prior art").

According to the above-mentioned prior art, as shown in FIGS. 1 and 2, a sub-lance 4 is fitted to a sub-lance carriage 2, rotatably around the axial line of said sub-lance 4 and releasably from the sub-lance carriage 2. The sub-lance carriage 2, which is suspended by a wire rope 5, is vertically movable together with the sub-lance 4 along a guide rail 41 provided on a turning frame 1, through guide rollers, by hoisting up or down the wire rope 5 through a winch (not shown). As shown in FIG. 1, a probe 42 for sampling and temperature-measuring of a molten metal during refining thereof is releasably fitted to the lowermost end of the sub-lance 4.

As shown in FIG. 2, the sub-lance 4 has a concentric three-pipe structure comprising from inside to outside a gas supply pipe 43, a water discharge pipe 44, and a water supply pipe 45.

Also as shown in FIG. 2, a water supply outer cylinder 48 rotatably engages with the upper end portion of said water supply pipe 45 through bearings 46 and 47. The bearing 46 is fitted to the upper end portion of the water supply outer cylinder 48, and the bearing 47 is fitted to the lower end portion of the water supply outer cylinder 48. The water supply pipe 45, the water supply outer cylinder 48 and the bearings 46 and 47 are assembled so as not to come off from each other by tightening a tightening nut 49 to the outer portion of the water supply pipe 45 at the lowermost end portion of the water supply outer cylinder 48. It is therefore possible to withdraw the water supply outer cylinder 48 downward from the water supply pipe 45, by removing the tightening nut 49 from the water supply pipe 45. The gap between the water supply outer cylinder 48 and the water supply pipe 45 is water tightly sealed by oil seals 50a, 50b, 50c and 50d at positions near the upper and lower ends of the bearing 46 and the upper and lower ends of the bearing 47. The water supply pipe 45 is provided with a plurality of water supply holes 51 along the circumference thereof. The plurality of water supply holes 51 communicate with an annular groove 52 provided between the outer surface of the water supply pipe 45 and the inner surface of the water supply outer cylinder 48. The water supply outer cylinder 48 is fitted with a water supply branch pipe 54 having a flange joint 53, for connecting an external cooling water supply pipe 70 having a flange joint 69. The water supply branch pipe 54 communicates with the annular groove 52. Cooling water can therefore be supplied from the external cooling water supply pipe 70 through the water supply branch pipe 54, the water supply outer cylinder 48, the annular groove 52, and the water supply holes 51 into the water supply pipe 45.

As shown in FIG. 2, as in the water supply pipe 45 mentioned above, a water discharge outer cylinder 57 rotatably engages with the upper end portion of the water discharge pipe 44 through bearings 55 and 56. The bearing 55 is fitted to the upper end portion of the water discharge outer cylinder 57, and the bearing 56 is fitted to the lower end portion of the water discharge outer cylinder 57. The water discharge pipe 44, the water discharge outer cylinder 57 and the bearings 55 and 56 are assembled so as not to come off from each other by tightening another tightening nut 58 to the outer portion of the water discharge pipe 44 at the lowermost end portion of the water discharge outer cylinder 57. It is therefore possible to withdraw the water discharge outer cylinder 57 downward from the water discharge pipe 44 by removing the tightening nut 58 from the water discharge pipe 44. The gap between the water discharge outer cylinder 57 and the water discharge pipe 44 is water-tightly sealed by oil seals 59a, 59b, 59c and 59d at positions near the upper and lower ends of the bearing 55 and the upper and lower ends of the bearing 56. The water discharge pipe 44 is provided with a plurality of water discharge holes 60 along the circumference thereof. The water discharge holes 60 communicate with another annular groove 61 provided between the outer surface of the water discharge pipe 44 and the inner surface of the water discharge outer cylinder 57. The water discharge outer cylinder 57 is fitted with a water discharge branch pipe 63 having a flange joint 62, for connecting an external cooling water discharge pipe 72 having a flange joint 71. The water discharge branch pipe 63 communicates with the annular groove 61. Therefore, cooling water, directed from the lower end portion of the water supply pipe 45 to the lower end of the water discharge pipe 44, can be discharged through the water discharge pipe 44, water discharge holes 60, the annular groove 61, the water discharge outer cylinder 57, the water discharge branch pipe 63, and the external cooling water discharge pipe 72, to outside. The sub-lance 4 is thus cooled by cooling water.

A probe 42 for sampling and temperature-measuring of molten metal is releasably fitted, as described above, to the lowermost end of the gas supply pipe 43, and a swivel joint 64 for connecting an external gas supply pipe (not shown) rotatably engages with the uppermost end thereof. To prevent slag from coming into the probe 42 when the probe 42 passes through the slag layer covering the surface of the molten metal, pressurized gas such as air and nitrogen gas is blown into the probe 42 from the external gas supply pipe (not shown) through the swivel joint 64 and the gas supply pipe 43. The swivel joint 64 is provided with a tapped hole 65 for taking out the lead wire of the probe.

As shown in FIG. 2, the gas supply pipe 43, the water discharge pipe 44 and the water supply pipe 45 constituting the sub-lance 4 are fixed to each other. More specifically, the gas supply pipe 43 is fixed at the lower end thereof by welding to the lower end of the water discharge pipe 44, and the water discharge pipe 44 is fixed by a bolt 67 to the water supply pipe 45. The upper end portion of the water discharge pipe 44 and the upper end portion of the gas supply pipe 45 are sealed by a gland packing 66.

As shown in FIG. 2, the flange joint 53 of the water supply branch pipe 54 and the flange joint 62 of the water discharge branch pipe 63 are connected by a fixing plate 68. Connection of the flange joint 53 and the flange joint 62 is effected as follows. The water supply branch pipe 54 and the water discharge branch pipe 63 are aligned so as to achieve agreement of their axial lines, and then, the flange joint 53 of the water supply branch pipe 54 and the flange joint 62 of the water discharge branch pipe 63 are tightly connected to the flange joint 69 of the external cooling water supply pipe 70 and the flange joint 71 of the external water discharge pipe 72 by bolts and nuts (not shown) with the fixing plate 68 in between. The external cooling water supply pipe 70 and the external cooling water discharge pipe 72 are connected through respective flexible hoses (not shown) to a water source. Therefore, the sub-lance carriage 2 and the sub-lance 4 fitted on the sub-lance carriage 2 smoothly move up and down along the vertical guide rail 41 of the turning frame 1.

Since, as mentioned above, the gas supply pipe 43, the water discharge pipe 44 and the water supply pipe 45 are integrally assembled, when the sub-lance 4 is rotated in a manner as described later around the axial line thereof, the gas supply pipe 43, the water discharge pipe 44 and the water supply pipe 45 also rotate as an integral entity. The water supply outer cylinder 48, the water discharge outer cylinder 57 and the swivel joint 64 rotatably engage respectively with the upper end portions of the water supply pipe 45, the water discharge pipe 44 and the gas supply pipe 43. Furthermore, since the water supply branch pipe 54 of the water supply outer cylinder 48 and the water discharge branch pipe 63 of the water discharge outer cylinder 57 are integrally connected by the fixing plate 68, the water supply outer cylinder 48 and the water discharge outer cylinder 57 are also integrally connected. In addition, as shown in FIG. 2, a pin 73 fixed to the lower surface of the water supply outer cylinder 48 engages with a pin hole (not shown) provided in a receiving stand fixed to the sub-lance carriage 2. When the sub-lance 4 is rotated, therefore, the water supply outer cylinder 48 and the water discharge outer cylinder 57 do not rotate together with the sub-lance 4, but stand still always at prescribed positions. Thus, water supply to, and water discharge from the sub-lance 4 are carried out with no trouble.

In FIG. 2, 74 is a drive mechanism including a reduction gear, fitted via a fitting rack 74a to the water discharge outer cylinder 57, for rotating the sub-lance 4 around the axial line thereof. A chain 77 engages with a small sprocket 75 fixed to the axle of rotation of the drive mechanism 74 and with a large sprocket 76 fixed to the upper end portion of the water discharge pipe 44, so that the sub-lance 4 may be rotated by a desired angle around the axial line thereof by operating the drive mechanism 74. A sub-lance rotation angle detector 79 including a synchro device is provided at the tip of the axle of rotation of the drive mechanism 74 through another fitting rack 78. The indication of the sub-lance rotation angle detector 79 permits easy and accurate detection of an angle of rotation of the sub-lance 4 from the original position of the sub-lance 4 before rotation. It is therefore possible to accurately rotate the sub-lance 4 by the most appropriate angle of rotation for correcting a deflection of the sub-lance 4 toward the main lance, which occurs during refining of a molten metal in a top-blowing oxygen converter.

In FIGS. 1 and 2, 80 is a suspension fitting fixed to the upper end portion of the water discharge outer cylinder 57. The sub-lance 4 is engaged with or disengaged from the sub-lance carrier 2 by hoisting up or down the suspension fitting 80 with the use of a crane (not shown). More specifically, the sub-lance 4 can be easily engaged with a sub-lance carriage 2 by inserting the sub-lance 4, by hoisting down with the use of the crane, into a notch in the receiving stand fixed to the upper end portion of the sub-lance carriage 2 and into an opening in a sub-lance supporting device 40 fixed to the lower end portion of the sub-lance carriage 2. The sub-lance 4 is easily removed from the sub-lance carriage 2 by hoisting up the sub-lance 4 thus fitted to the sub-lance carriage 2 with the use of the crane, from the notch in the receiving stand and the opening in the sub-lance supporting device 40. The sub-lance supporting device 40 has the function, in cooperation with the receiving stand fixed to the upper end portion of the sub-lance carriage 2, of ensuring alignment for holding the sub-lance 4 substantially vertically, and of preventing the sub-lance 4 from swinging.

The sub-lance assembly of the prior art described above has the following excellent advantages providing remarkable effects:

(a) Possibility of easy and accurate detection of the angle of rotation of the sub-lance 4 ensures correction of a deflection of the sub-lance 3 toward the main lance, which occurs during refining of molten metal in a top-blowing oxygen converter. As a result, while it was necessary to replace twelve sub-lances for 1,000 repetitions of sampling and/or temperature-measuring in the conventional sub-lance assembly, it is not necessary, according to the prior art, to make any replacement of sub-lance for the same number of repetitions of sampling and/or temperature-measuring, and sampling and/or temperature-measuring can be effected in satisfactory condition; and, (b) Easy alignment adjustment is ensured for holding the sub-lance 4 accurately in the vertical position, and in addition, prevention of the sub-lance from swinging is ensured.

However, the prior art involves the following problems:

(1) The water supply branch pipe 54 and the water discharge branch pipe 63 are integrally connected by the fixing plate 68, and the water supply branch pipe 54 and the water discharge branch pipe 63 are respectively connected, via the fixing plate 68, to the external cooling water supply pipe 70 and the external cooling water discharge pipe 72. In order to prevent cooling water from leaking at the above-mentioned connections, it is necessary not only to conduct accurate alignment of the constitutent components 54, 63, 68, 70 and 72, but also to uniformly tighten the above-mentioned connections, thus requiring a considerable time. Furthermore, if these connections are not properly effected, strong non-uniform forces act on the bearing and oil seal mechanisms between the water supply pipe 45 and the water supply outer cylinder 48, as well as between the water discharge pipe 44 and the water discharge outer cylinder 57, thus not only impairing smooth rotation of the sub-lance 4, but also resulting in a trouble of the oil seal mechanisms, which may lead to a serious accident of cooling water leakage.

(2) The weight of the external cooling water supply pipe 70 and the flexible hose connected to the external cooling water supply pipe 70, as well as the weight of the external cooling water discharge pipe 72 and the flexible hose connected to the external cooling water discharge pipe 72 are applied to the water supply branch pipe 54, the water supply outer cylinder 48, the water discharge branch pipe 63 and the water discharge outer cylinder 57, thus rendering the problem described in (1) above more serious.

(3) The water supply outer cylinder 48 rotatably engages with the water supply pipe 45, and the water discharge outer cylinder 57 rotatably engages with the water discharge pipe 44. This increases the assembling time and labor of the sub-lance assembly, and requires more complicated maintenance and inspection of the sub-lance assembly.

(4) Because of the many seal mechanisms such as oil seals, the reliability of sealing against cooling water decreases accordingly.

For these reasons, the prior art, while having the above-mentioned excellent advantages, involved problems not permitting full utilization of such advantages.

SUMMARY OF THE INVENTION

An object of the present invention is therefore to provide an improved sub-lance assembly for sampling and temperature-measuring of a molten metal during refining thereof in a top-blowing oxygen converter, which can be used many times.

Another object of the present invention is to provide an improved sub-lance assembly including a sub-lance rotatable around the axial line thereof.

A principal object of the present invention is to provide an improved sub-lance assembly including a sub-lance rotatable around the axial line thereof, said improved sub-lance assembly permitting smooth rotation of the sub-lance, sure prevention of leakage of cooling water through avoidance of non-uniform forces acting on the seal mechanisms against cooling water for cooling the sub-lance assembly, prevention of the decrease in the reliability of sealing against cooling water, prevention of the increase in assembling time and labor, and easy maintenance and inspection.

In accordance with one of the features of the present invention, in a sub-lance assembly for sampling and temperature-measuring of a molten metal during refining thereof, which comprises:

a sub-lance having a concentric three-pipe structure comprising a gas supply pipe, a water supply pipe and a water discharge pipe with said gas supply pipe as the center, said gas supply pipe, said water supply pipe and said water discharge pipe being assembled by being fixed to each other, said sub-lance being rotatably and releasably fitted to a sub-lance carriage in the substantially vertical position by a receiving stand fixed to the upper end portion of said sub-lance carriage and a sub-lance supporting device fixed to the lower end portion of said sub-lance carriage, said sub-lance carriage being adapted to move up and down along a guide rail provided vertically on a turning frame;

a probe, releasably fitted to the lowermost end of said gas supply pipe, for sampling and temperature-measuring of the molten metal during refining thereof;

a drive mechanism for rotating said sub-lance around the axial line thereof; and, a sub-lance rotation angle detector, fitted to the tip of the axle of said drive mechanism, said sub-lance rotation angle detector being adapted to detect the angle of rotation of said sub-lance;

there is provided the improvement comprising:

an inner cylinder fixed to the upper end portion of said sub-lance, the uppermost ends of said water supply pipe and said water discharge pipe being closed by said inner cylinder, the lowermost end portions of said water supply pipe and said water discharge pipe communicating with each other in a water-tight manner, the uppermost end of said gas supply pipe projecting above said inner cylinder; and, an outer cylinder, having a water supply branch pipe and a water discharge branch pipe, rotatably engaging with said inner cylinder through a bearing mechanism and a sealing mechanism, said water supply pipe, said inner cylinder, said outer cylinder and said water supply branch pipe communicating with each other in a water-tight manner, said water discharge pipe, said inner cylinder, said outer cylinder and said water discharge branch pipe communicating with each other in a water-tight manner, and, said outer cylinder being connected to said sub-lance carriage, to prevent said outer cylinder from rotating together with said sub-lance and said inner cylinder when said sub-lance is rotated together with said inner cylinder by means of said drive mechanism.

BRIEF DESCRIPTION OF THE DRAWINGS

FIG. 1 is a schematic drawing illustrating an example of fitting and vertical movement of the sub-lance assembly of the prior art;

FIG. 5 is a partially cutaway plan view illustrating an embodiment of the sub-lance assembly of the present invention.

DETAILED DESCRIPTION OF PREFERRED EMBODIMENTS

Figure 2:
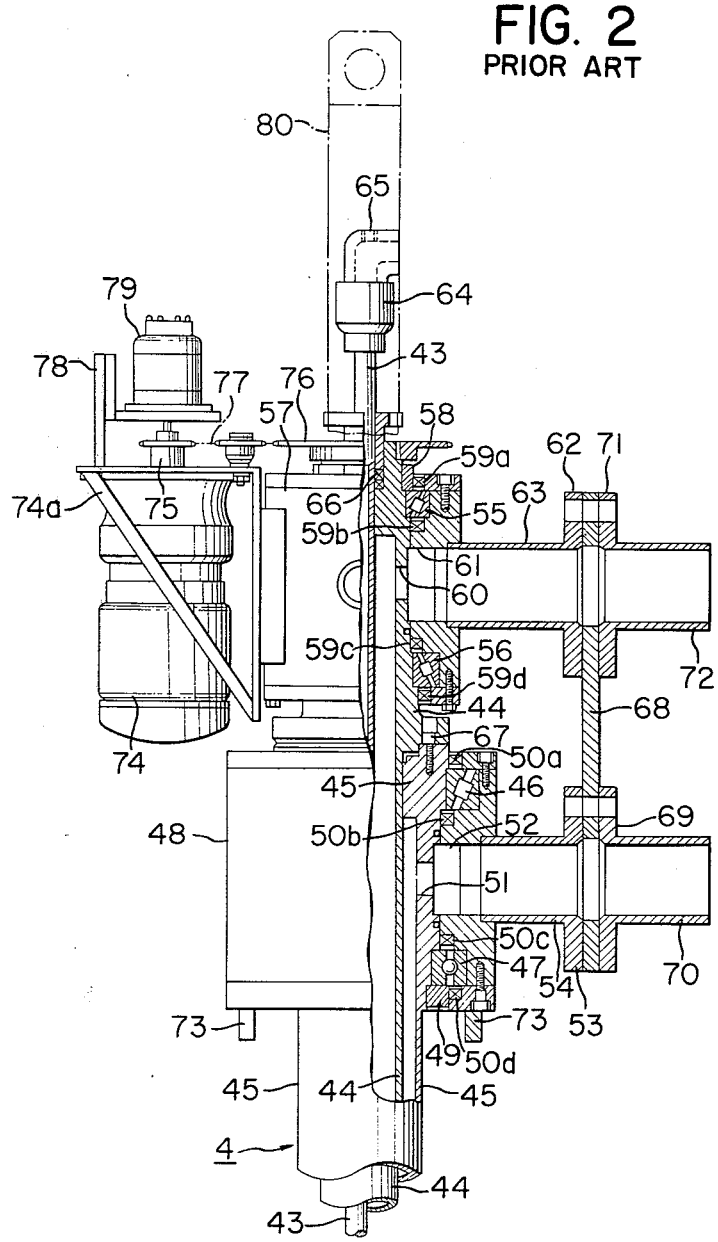
FIG. 2 is a partially cutaway front view of the sub-lance assembly of the prior art.

We conducted intensive studies to solve the above-mentioned problems involved in the prior art, and obtained as a result the following findings:

(1) The water supply outer cylinder 48 and the water discharge outer cylinder 57 in the sub-lance assembly of the prior art are mutually independently rotatable relative to the sub-lance 4, whereas the water supply outer cylinder 48 and the water discharge outer cylinder 57 should be integrally rotated relative to the sub-lance 4. In the prior art, therefore, the water supply branch pipe 54 of the water supply outer cylinder 48, the external cooling water supply pipe 70, the water discharge branch pipe 63 of the water discharge outer cylinder 57, and the external cooling water discharge pipe 72 are integrally connected via the fixing plate 68. Because of this arrangement of the prior art, as mentioned previously, not only assembling operation of these constituent components requires much time, but also the assembling operation, if not conducted accurately, often leads to such inconveniences as impaired rotation of the sub-lance 4 and leakage of cooling water.

(2) Therefore, by replacing the two rotatable constituent components, i.e., the water supply outer cylinder 48 and the water discharge outer cylinder 57, by a single rotatable constituent component, and fixing the water supply branch pipe 54 and the water discharge branch pipe 63 to said single rotatable constituent component, it is possible to omit complicated assembling operation using the fixing plate 68 as in the prior art, and in addition, to avoid occurrence of such inconveniences as impared rotation of the sub-lance 4 and leakage of cooling water.

The present invention was made on the basis of the above-mentioned findings, and the sub-lance assembly of the present invention for sampling and temperature-measuring of a molten metal during refining thereof comprises:

a sub-lance having a concentric three-pipe structure comprising a gas supply pipe, a water supply pipe and a water discharge pipe with said gas supply pipe as the center, said gas supply pipe, said water supply pipe and said water discharge pipe being assembled by being fixed to each other, said sub-lance being rotatably and releasably fitted to a sub-lance carriage in the substantially vertical position by a receiving stand fixed to the upper end portion of said sub-lance carriage and a sub-lance supporting device fixed to the lower end portion of said sub-lance carriage, said sub-lance carriage being adapted to move up and down along a guide rail provided vertically on a turning frame;

a probe, releasably fitted to the lowermost end of said gas supply pipe, for sampling and temperature-measuring of the molten metal during refining thereof;

a drive mechanism for rotating said sub-lance around the axial line thereof; and, a sub-lance rotation angle detector, fitted to the tip of the axle of said drive mechanism, said sub-lance rotation angle detector being adapted to detect the angle of rotation of said sub-lance;

said sub-lance assembly being characterized by comprising:

an inner cylinder fixed to the upper end portion of said sub-lance, the uppermost ends of said water supply pipe and said water discharge pipe being closed by said inner cylinder, the lowermost end portions of said water supply pipe and said water discharge pipe communicating with each other in a water-tight manner, the uppermost end of said gas supply pipe projecting above said inner cylinder; and, an outer cylinder, having a water supply branch pipe and a water discharge branch pipe, rotatably engaging with said inner cylinder through a bearing mechanism and a sealing mechanism, said water supply pipe, said inner cylinder, said outer cylinder and said water supply branch pipe communicating with each other in a water-tight manner, said water discharge pipe, said inner cylinder, said outer cylinder and said water discharge branch pipe communicating with each other in a water-tight manner, and, said outer cylinder being connected to said sub-lance carriage, to prevent said outer cylinder from rotating together with said sub-lance and said inner cylinder when said sub-lance is rotated together with said inner cylinder by means of said drive mechanism.

Now, the sub-lance assembly of the present invention for sampling and temperature-measuring of a molten metal during refining thereof is described in detail by means of an example with reference to the drawings.

EXAMPLE

Figure 3:
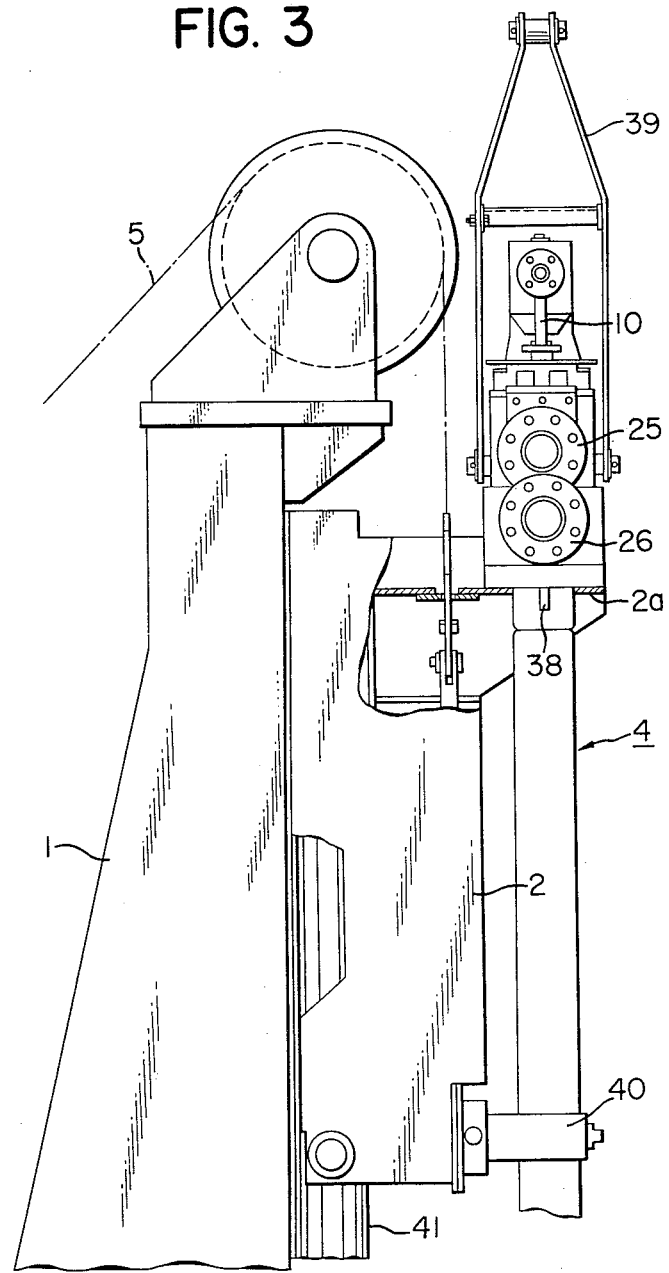
FIG. 3 is a partially cutaway side view illustrating an embodiment of the sub-lance assembly of the present invention.
Figure 4:
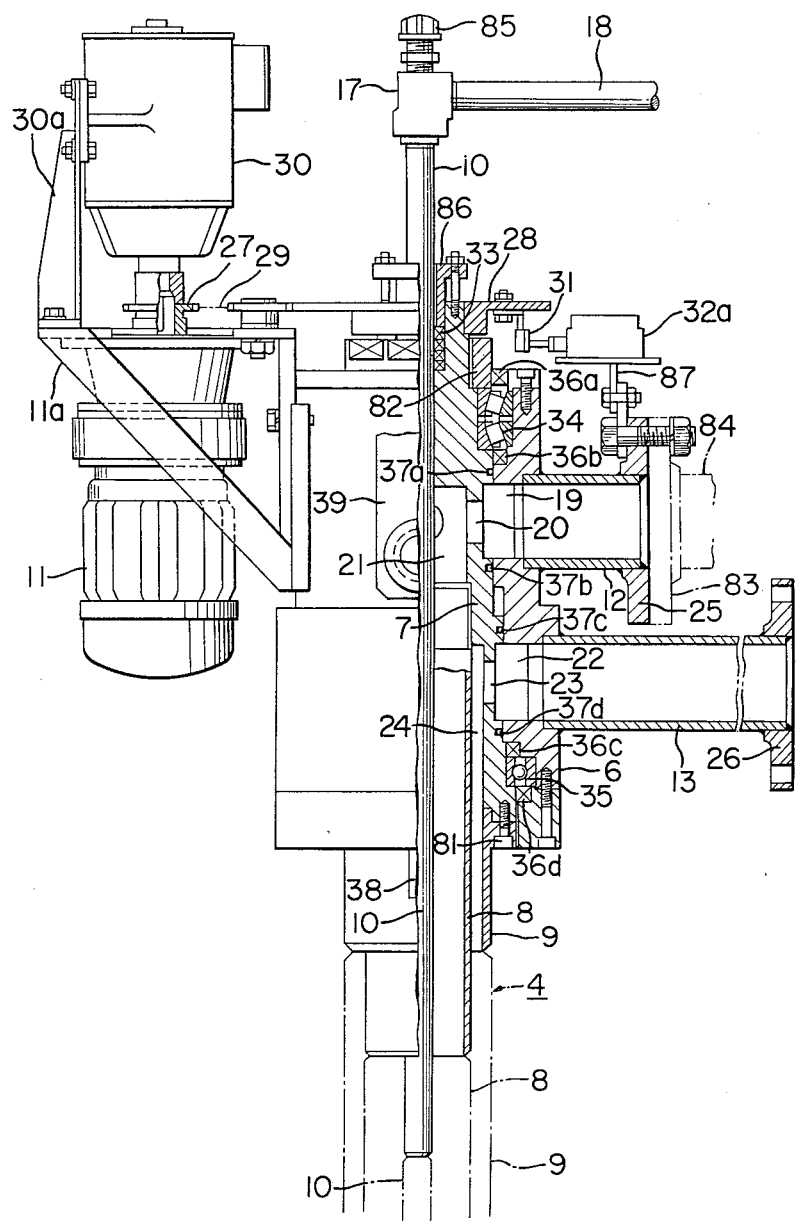
FIG. 4 is a partially cutaway front view illustrating an embodiment of the sub-lance assembly of the present invention.

FIG. 3 is a partial cutaway side view illustrating an embodiment of the sub-lance assembly of the present invention, and FIG. 4 is a partial cutaway front view of same.

In FIGS. 3 and 4, 4 is a sub-lance, 1 is a turning frame, and 2 is a sub-lance carriage. The sub-lance 4 is rotatably and releasably fitted to the sub-lance carriage 2, as described later, by a receiving stand 2a and a sub-lance supporting device 40 both fixed to the sub-lance carriage 2. The sub-lance carriage 2 is suspended by a wire rope 5, and is vertically movable together with the sub-lance 4 along a guide rail 41 provided on a turning frame 1 by hoisting up or down said wire rope 5 with the use of a winch (not shown). As described previously with reference to FIG. 1, a probe for sampling and temperature-measuring of a molten metal during refining thereof is releasably fitted to the lowermost end of the sub-lance 4. Sampling and temperature-measuring of the molten metal are therefore carried out by lowering the sub-lance 4 together with the sub-lance carriage 2 by hoisting down the wire rope 5 with the use of the winch at the time of sampling and temperature-measuring of the molten metal in the converter, and by immersing the probe fitted to the lowermost end of the sub-lance 4 into the molten metal. As has conventionally been known, the sub-lance 4 can be moved, as required, together with the sub-lance carriage 2 from outside to above the converter and from above the converter to outside, by turning the turning frame 1.

As shown in FIGS. 3 and 4, the sub-lance 4 has a concentric three-pipe structure comprising from inside to outside a gas supply pipe 10, a water supply pipe 8 and a water discharge pipe 9. The gas supply pipe 10, the water supply pipe 8 and the water discharge pipe 9 are integrally assembled by being fixed to each other as described later to form the sub-lance 4.

In FIG. 4, 7 is an inner cylinder, and 6 is an outer cylinder. As described later, the inner cylinder 7 is fixed to the upper end portion of the sub-lance 4, and the inner cylinder 7 rotatably engages in the outer cylinder 6. More specifically, the upper end portion of the water discharge pipe 9 is fixed by a bolt 81 to the lower portion of the inner cylinder 7, and the upper end portion of the water supply pipe 8 is fixed to the center portion of the inner surface of the inner cylinder 7 by screwing. The upper end portion of the gas supply pipe 10 projecting above the inner cylinder 7 is fixed to the uppermost end portion of the inner cylinder 7 by a gland packing 33 and a shrouding member 86. The lowermost end portions of the gas supply pipe 10, the water supply pipe 8 and the water discharge pipe 9 are fixed to each other by welding. The lowermost end portion of the water supply pipe 8 communicates with the lowermost end portion of the water discharge pipe 9.

The inner cylinder 7 rotatably engages in the outer cylinder 6 through an upper bearing 34 and a lower bearing 35. The inner cylinder 7, the outer cylinder 6, the upper bearing 34 and the lower bearing 35 are assembled so as not to come off from each other by tightening a tightening nut 82. It is therefore possible to easily remove the outer cylinder 6 from the inner cylinder 7 by removing the tightening nut 82. This forms one of the features of the sub-lance assembly of the present invention. More particularly, since the outer cylinder 6 provided with a water supply branch pipe and a water discharge branch pipe as described later can be easily removed from the inner cylinder 7 by removing the tightening nut 82, such operations as (a) assembling of the sub-lance assembly, (b) maintenance, inspection, or replacement of the sub-lance, and (c) maintenance, inspection or replacement of bearing mechanisms 34 and 35 provided between the inner cylinder 7 and the outer cylinder 6 and of seal mechanisms described later provided between the inner cylinder 7 and the outer cylinder 6, can be effected easily and in a short period of time.

As shown in FIG. 4, the gap between the outer surface of the inner cylinder 7 and the inner surface of the outer cylinder 6 is sealed in a water-tight manner by oil seals 36a and 36b arranged on top and bottom of the upper bearing 34 and oil seals 36c and 36d arranged on top and bottom of the lower bearing 35.

A water supply branch pipe 12 having a flange joint 25 for connecting an external cooling water supply pipe 84 (a portion shown in FIG. 4) is fixed to the upper portion of the outer surface of the outer cylinder 6, and a water discharge branch pipe 13 having a flange joint 26 for connecting an external cooling water discharging pipe (not shown) is fixed to the lower portion of the outer surface of the outer cylinder 6.

The water supply branch pipe 12 communicates with a first annular groove 19 provided between the inner surface of the outer cylinder 6 and the outer surface of the inner cylinder 7. The gap between the inner surface of the outer cylinder 6 and the outer surface of the inner cylinder 7, where the first annular groove 19 is provided, is sealed by O-rings 37a and 37b arranged on top and bottom of the first annular groove 19. The first annular groove 19 communicates with a plurality of water supply holes 20 provided in the inner cylinder 7 along the circumference thereof. The plurality of water supply holes 20 communicate with the uppermost end of the water supply pipe 8 through a first space 21 provided in the inner cylinder 7. Therefore, since the external cooling water supply pipe 84, the water supply branch pipe 12, the first annular groove 19, the water supply holes 20, the sapce 21 and the water supply pipe 8 communicate with each other in a water-tight manner, cooling water is supplied from a water source (not shown), through the external cooling water supply pipe 84, the water supply branch pipe 12, the first annular groove 19, the water supply holes 20 and the first space 21, into the water supply pipe 8.

The water discharge branch pipe 13 communicates with a second annular groove 22 provided between the inner surface of the outer cylinder 6 and the outer surface of the inner cylinder 7. The gap between the inner surface of the outer cylinder 6 and the outer surface of the inner cylinder 7, where the second annular groove 22 is provided, is sealed by O-rings 37c and 37d arranged on top and bottom of the second annular groove 22. The second annular groove 22 communicates with a plurality of water discharge holes 23 provided in the inner cylinder 7 along the circumference thereof. The plurality of water discharge holes 23 communicate with the uppermost end of the water discharge pipe 9 through a second space 24 provided in the inner cylinder 7. Therefore, since the external cooling water discharge pipe (not shown), the water discharge branch pipe 13, the second annular groove 22, the water discharge holes 23, the second space 24 and the water discharge pipe 9 communicate with each other in a water-tight manner, and the lowermost end portion of the water supply pipe 8 communicates with the lowermost end portion of the water discharge pipe 9, the cooling water supplied into the water supply pipe 8 is discharged through the water discharge pipe 9, the second space 24, the water discharge holes 23, the second annular groove 22, the water discharge branch pipe 13 and the external cooling water discharge pipe to outside. Thus, the sub-lance 4 is cooled by cooling water.

As shown in FIG. 4, a swivel joint 17 rotatably engages with the uppermost end of the gas supply pipe 10. An external gas supply pipe 18 is connected to the swivel joint 17. As described previously, a probe (not shown) for sampling and temperature-measuring of a molten metal during refining thereof, is releasably fitted to the lowermost end of the gas supply pipe 10. To prevent slag from coming into the probe when the probe passes through the slag layer covering the surface of the molten metal, a pressurized gas such as air and nitrogen gas is blown into the probe from the external gas supply pipe 18 through the swivel joint 17 and the gas supply pipe 10. The swivel joint 17 is provided with a tapped hole (not shown) for taking out the lead wire of the probe, and the tapped hole is sealed by a cap 85.

The external cooling water supply pipe 84 and the external cooling water discharge pipe are connected to a water source respectively through flexible hoses (not shown), and the external gas supply pipe 18 is connected to a gas reservoir (not shown) through another flexible hose. Therefore, the sub-lance carriage 2 and the sub-lance 4 fitted to the sub-lance carriage 2 smoothly move up and down along the guide rail 41 of the turning frame 1.

As describe above, the gas supply pipe 10, the water supply pipe 8 and the water discharge pipe 9, which constitute the sub-lance 4, are assembled by being fixed to each other, the inner cylinder 7 is fixed to the upper end portion of the sub-lance 4, and the inner cylinder 7 rotatably engages in the outer cylinder 6. Therefore, when rotating the sub-lance 4 as described later, the inner cylinder 7 rotates together with the sub-lance 4, whereas the outer cylinder 6 does not rotate together with the sub-lance 4 and the inner cylinder 7, but stands still always at a prescribed position. In this example, as shown in FIGS. 3 and 4, a pin 38 is fixed by welding to the lower surface of the outer cylinder 6. When the sub-lance 4 is fitted to the sub-lance carriage 2, the pin 38 engages with a pin hole (not shown) provided in the receiving stand 2a which is fixed to the sub-lance carriage 2, and thus more surely prevents the outer cylinder 6 from rotating together with the sub-lance 4 and the inner cylinder 7.

In FIG. 4, 11 is a drive mechanism including a reduction gear for rotating the sub-lance 4 around the axial line thereof. The drive mechanism 11 is fitted onto the outer side surface of the outer cylinder 6 through a fitting rack 11a. A chain 29 engages with a small sprocket 27 fixed to the axle of rotation of the drive mechanism 11 and with a large sprocket 28 fixed onto the upper surface of the inner cylinder 7 so that the sub-lance 4 may be rotated by a desired angle around the axial line thereof by operating the drive mechanism 11. A sub-lance rotation angle detector 30 including a synchro device is provided at the tip of the axile of rotation of the drive mechanism 11 through another fitting rack 30a. The indication of the sub-lance rotation angle detector 30 permits easy and accurate detection of an angle of rotation of the sub-lance 4 from the original position of the sub-lance 4 before rotation. Indication of the sub-lance rotation angle detector may well be based for example on a dial having a 360° calibration and a pointer, or on the recording on a charge paper. The actuation of the drive mechanism 11 can be automatically controlled by previously setting the sub-lance rotation angle detector 30 at a prescribed angle of rotation of the sub-lance 4, and when the sub-lance 4 rotates by the prescribed angle, feeding back a signal to the drive mechanism 11.

In FIGS. 4 and 5, 31 is a striker fixed to the lower surface of the large sprocket 28, and 32a and 32b are a pair of limit switches fitted close to each other on further another fitting rack 87, fixed by welding to the water supply pipe 12. The pair of limit switches 32a and 32b are actuated by being pushed by the striker 31 to prevent the sub-lance 4 from rotating by more than one turn in the same direction, thus preventing the lead wire of the probe, inserted into the gas supply pipe 10, from twisting or twisting off. The striker 31, which has only to rotate together with the inner cylinder 7, may be fixed to the inner cylinder 7 at an appropriate position, and, because the striker 31 has only to rotate together with the outer cylinder 6, it may be fixed to the outer cylinder 6 at an appropriate position.

Actuation of the striker 31 and the pair of limit switches 32a and 32b is as follows. In FIGS. 4 and 5, when the sub-lance 4 rotates together with the large sprocket 28 rotating counter-clockwise, and the striker 31 reaches the position shown by the single-point chain line 31a, the limit switch 32a is actuated by being pushed by the striker 31. This causes the drive mechanism 11 to stop, and thus the sub-lance 4 stops rotating. On the other hand, when the sub-lance 4 rotates together with the large sprocket 28 rotating clockwise, and the striker 31 reaches the position shown by the two-point chain line 31b, the limit switch 32b is actuated by being pushed by the stricker 31. This causes the drive mechanism 11 to stop, and thus the sub-lance 4 stops rotating. Since the sub-lance 4 does not rotate by more than one turn in the same direction as mentioned above, the sub-lance 4 never rotates by multiple turns in the same direction by an erroneous operation, thus preventing the lead wire of the probe, inserted into the gas supply pipe 10, from twisting or twisting off.

In FIGS. 3 and 4, 39 is a suspension fitting fitted to the upper portion of the outer cylinder 6. In the same manner as described with respect to the prior art, the sub-lance 4 is engaged with or disengaged from the sub-lance carriage 2 by hoisting up or down the suspension fitting 39 with the use of a crane (not shown). More specifically, the sub-lance 4 can be easily engaged with the sub-lance carriage 2 by inserting the sub-lance 4, by hoisting down with the use of the crane, into a notch in the receiving stand 2a fixed to the upper end portion of the sub-lance carriage 2 and into an opening in the sub-lance supporting device 40 fixed to the lower end portion of the sub-lance carriage 2. The sub-lance 4 can be easily removed from the sub-lance carriage 2 by hoisting up the sub-lance 4 thus fitted to the sub-lance carriage 2 with the use of the crane.

In the above-mentioned example, the sub-lance 4 having the concentric three-pipe structure comprising from inside to outside the gas supply pipe 10, the water supply pipe 8 and the water discharge pipe 9 have been used, however, a sub-lance having a concentric three-pipe structure comprising from inside to outside a gas supply pipe, a water discharge pipe and a water supply pipe may be used. In the latter case, the only difference is that cooling water is supplied from the water discharge branch pipe 13 of the former case, and cooling water is discharged from the water supply branch pipe 12 of the former case (in other words, only the flow direction of cooling water is reversed), and the sub-lance structure in the latter case is just the same as the sub-lance structure in the former case.

According to the sub-lance assembly of the present invention, as described above in detail, the following industrially useful effects are provided:

(a) In the sub-lance assembly of the prior art, it is necessary to integrally connect two independently rotatable cylinders, i.e., the water supply outer cylinder 48 and the water discharge outer cylinder 57 by the fixing plate 68, thus requiring complicated assembly operations and much time. In the sub-lance assembly of the present invention, in contrast, the only rotatable cylinder is the outer cylinder 6, leading to simpler assembling operations and a shorter time required.

(b) In the sub-lance assembly of the prior art, assembling of the water supply branch pipe 54, the water discharge branch pipe 63, the fixing plate 68, the external cooling water supply pipe 70 and the external cooling water discharge pipe 72, if not carried out correctly, results in strong non-uniform forces acting on the bearing mechanism and the seal mechanism, thus not only impairing smooth rotation of the sub-lance 4, but also leading to a trouble of the seal mechanism, which may result in a serious accident of cooling water leakage. In the sub-lance assembly of the present invention, in contrast, since both the water supply branch pipe 12 and the water discharge branch pipe 13 are fixed to the outer cylinder 6, it is not necessary to align the constituent components, and strong non-uniform forces never act on the bearing and seal mechanisms. The sub-lance therefore always smoothly rotates, and there is no risk of cooling water leakage caused by a trouble of the seal mechanism.

(c) While the sub-lance assembly of the prior art has two rotatable cylinders, the sub-lance assembly of the present invention has only one rotatable cylinder. The sealing effectiveness against cooling water for the sub-lance assembly of the present invention is therefore higher than that for the sub-lance assembly of the prior art.

(d) The number of bearing and seal mechanisms in the sub-lance assembly of the present invention is a half that in the sub-lance assembly of the prior art, making it so much easier to conduct maintenance and inspection.

What is claimed is:

1. In a sub-lance assembly for sampling and temperature-measuring of a molten metal during refining thereof, which comprises:
a sub-lance (4) having a concentric three-pipe structure comprising a gas supply pipe (10), a water supply pipe (8) and a water discharge pipe (9) with said gas supply pipe as the center pipe, said gas supply pipe, said water supply pipe and said water discharge pipe being assembled and fixed to each other, said sub-lance being rotatably and releasably fitted to a sub-lance carriage (2) in the substantially vertical position by a receiving stand fixed to the upper end portion of said sub-lance carriage and a sub-lance supporting device fixed to the lower end portion of said sub-lance carriage, said sub-lance carriage being adapted to move up and down along a guide rail provided vertically on a turning frame;
a probe, releasably fitted to the lowermost end of said gas supply pipe, for sampling and temperature-measuring of the molten metal during refining thereof;

a drive mechanism for rotating said sub-lance around the axial line thereof; and a sub-lance rotation angle detector, fitted to the tip of the axle of said drive mechanism, said sub-lance rotation angle detector being adapted to detect the angle of rotation of said sub-lance;

the improvement comprising:

an inner cylinder (7) defining a first space (21) and a second space (24) therein and having a plurality of water supply holes (20) provided along the circumference thereof in communication with said first space (20) and a plurality of water discharge holes (23) in communication with said second space (24), said inner cylinder (7) being fixed to the upper end portion of said sub-lance (4), the uppermost end of said water supply pipe (8) being removably connected to said inner cylinder (7) and water-tightly communicating with said first space (21) in said inner cylinder (7), said first space (21) water-tightly communicating with said plurality of water supply holes (20) provided along the circumference of said inner cylinder (7), the uppermost end of said water discharge pipe (9) being removably connected to said inner cylinder (7) and water-tightly communicating with said second space (24), said second space (24) being located between said inner cylinder (7) and said water supply pipe (8) and water-tightly communicating with said plurality of water discharge holes (23), the lowermost end portions of said water supply pipe (8) and said water discharge pipe (9) water-tightly communicating with each other, the uppermost end of said gas supply pipe (10) projecting above said inner cylinder (7);

an outer cylinder (6) including a water supply branch pipe (12) and a water discharge branch pipe (13) fixedly mounted to said outer cylinder (6), said outer cylinder (6) rotatably engaging said inner cylinder (7) through bearing means (34,35) and sealing means (36a–36d), said outer cylinder (6) being connected to said sub-lance carriage (2) to prevent said outer cylinder (6) from rotating together with said sub-lance (4) and said inner cylinder (7) when said sub-lance (4) is rotated together with said inner cylinder (7) by means of said drive mechanism (11); and a first annular groove (19) and a second annular groove (22) provided between the inner surface of said outer cylinder (6) and the outer surface of said inner cylinder (7), said first annular groove (19) water-tightly communicating with said plurality of water supply holes (20) and said water supply branch pipe (12), and said second annular groove (22) water-tightly communicating with said plurality of water discharge holes (23) and said water discharge branch pipe (13):

whereby cooling water is directed through said water supply branch pipe (12), said first annular groove (19), said plurality of water supply holes (20) and said first space (21) into said water supply pipe (8), and then discharged through said water discharge pipe (9), said second space (24), said plurality of water discharge holes (23), said second annular groove (22) and said water discharge branch pipe (13) to the outside.

2. The sub-lance assembly of claim 1, wherein said concentric three-pipe structure of said sub-lance comprises from inside to outside a gas supply pipe, a water supply pipe and a water discharge pipe.

3. The sub-lance assembly of claim 1, wherein said concentric three-pipe structure of said sub-lance comprises from inside to outside a gas supply pipe, a water discharge pipe and a water supply pipe.

4. The sub-lance assembly of any one of claims 1–3, further comprising:

a pair of limit switches fixed to said inner cylinder fixed to said sub-lance; and a striker fixed to said outer cylinder to rotate together with said inner cylinder and said sub-lance;

said pair of limit switches being actuated by said striker rotating together with said inner cylinder and sub-lance to stop said drive mechanism, thus preventing said sub-lance from rotating by more than one turn in the same direction.

* * * * *